(12) United States Patent
Richter et al.

(10) Patent No.: US 11,808,713 B2
(45) Date of Patent: Nov. 7, 2023

(54) SYSTEM FOR DETECTING PATHOGENS IN PRODUCTS

(71) Applicants: Wolfgang Richter, Vancouver (CA);
Faranak Zadeh, Vancouver (CA)

(72) Inventors: Wolfgang Richter, Vancouver (CA);
Faranak Zadeh, Vancouver (CA)

(73) Assignee: EPIC SEMICONDUCTORS INC, Vancouver (CA)

( * ) Notice: Subject to any disclaimer, the term of this patent is extended or adjusted under 35 U.S.C. 154(b) by 266 days.

(21) Appl. No.: 17/389,962

(22) Filed: Jul. 30, 2021

(65) Prior Publication Data

US 2022/0034819 A1    Feb. 3, 2022

Related U.S. Application Data

(60) Provisional application No. 63/058,759, filed on Jul. 30, 2020.

(51) Int. Cl.
*G01N 21/84*   (2006.01)
*G01N 33/02*   (2006.01)
*G06N 20/00*   (2019.01)

(52) U.S. Cl.
CPC ......... *G01N 21/8483* (2013.01); *G01N 33/02* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 9,870,687 B1* | 1/2018 | Richter | H04Q 9/00 |
| 2012/0089117 A1* | 4/2012 | Junginger | A61M 37/0015 |
| | | | 604/173 |
| 2012/0112828 A1* | 5/2012 | Richter | H02J 50/05 |
| | | | 327/564 |
| 2013/0011332 A1* | 1/2013 | Boyden | B26F 1/24 |
| | | | 424/9.1 |
| 2014/0247152 A1* | 9/2014 | Proud | A61B 5/002 |
| | | | 340/870.07 |
| 2015/0180934 A1* | 6/2015 | Richter | G05B 19/102 |
| | | | 709/217 |
| 2016/0278639 A1* | 9/2016 | Proud | H04B 5/0037 |
| 2018/0039892 A1* | 2/2018 | Richter | G06F 15/76 |
| 2018/0067100 A1* | 3/2018 | Richter | G01N 27/60 |
| 2022/0023605 A1* | 1/2022 | Zvezdin | A61K 9/0021 |

* cited by examiner

*Primary Examiner* — Lore R Jarrett (57) ABSTRACT

An ion-jet electron-entangled pathogens analyzer imprinted on a test strip resembles the functionality of a scanning tunneling microscope as a hand-held device, to quickly detect pathogens in water and food products on their bio-electrical signature. The use of such a device does not require special training or preparation. The test strip consists of an integrated circuit which gets energized and communicates over a weak alternating electric field provided by a matchbox-sized base station, which also contains a trained machine learning module of bioelectrical pathogen signatures. The base station connects wirelessly to smart devices or networks for further processing or recording the measurement results in a blockchain. The base station can be worn as a smartwatch or attached to processing machines, transportation vehicles, warehouses, shelves and grocery stores.

14 Claims, 3 Drawing Sheets

SYSTEM FOR DETECTING PATHOGENS IN PRODUCTS

CROSS-REFERENCE TO RELATED APPLICATION

The present application claims benefit of priority from U.S. Provisional Application No. 63/058,759, filed Jul. 30, 2020, which is incorporated herein by reference in its entirety.

BACKGROUND OF THE INVENTION

1. Field of the Invention

The present invention generally relates a system for detecting pathogens in products, and more particularly relates to a system for detecting pathogens in products using an ion jet electron-entangled analyzer.

2. Description of Related Art

The use of field-deployable devices can reduce risk in the production of safe and sustainable foods by detecting food borne pathogens in several aspects in the "farm-to-fork" continuum. The current gold-standard method for detecting foodborne pathogens is the culture-based bacterial isolation and identification, but the procedures are tedious and time-consuming (2-3 days).

Many new methods have emerged for the rapid diagnosis of bacterial infections, including real-time polymerase chain reaction (PCR), DNA microarrays, and enzyme-linked immunosorbent assays (ELISAs). Real-time PCR and DNA microarrays allow the multiplex detection of bacteria with high sensitivity, but rely on complex sample pre-treatment and expensive instrumentation.

ELISAs are a widely used immunological approach that is less complicated and less expensive; however, it is still difficult to realize direct applications in the field because of the dependence on equipment and professional operation. Therefore, these techniques do not meet the criteria for the urgently needed on-site multiplex detection system for foodborne pathogens.

To evaluate the safety of food products analysts are required to conduct extensive testing that often take days to obtain a final test result. Having field deployable, rapid, sensitive, and specific testing methodologies would enable industry stakeholders to better protect consumers, provide a safer food supply, and meet international standards for exports.

With such devices, the food industry may increase the number of pathogen tests and may better prevent the presence of contaminated products from reaching the market place. Therefore, there is a need of a system and a method for scanning microorganisms in seconds supported by redundant spectroscopic measures to detect food borne pathogenic bacteria from samples taken from food production and processing facilities, as well as food products that require minimal processing such as leafy greens, fruits, and vegetables, using ion jet technology.

Further, the system should disclose a robust field-deployable diagnostic tool deployable in processing and production settings without the need for supporting equipment (i.e. incubators, centrifuges) and a fully functional laboratory with a minimum training. Further, the system should disclose detection of various type of bacteria such as *Salmonella* sp., *Listeria monocytogenes* and Verotoxigenic *E. coli* including O157:H7 in leafy greens such as lettuce or spinach.

SUMMARY OF THE INVENTION

In accordance with teachings of the present invention, a system for detecting pathogens in an object is provided.

An object of the present invention is to provide a system for detecting pathogens in an object. The object is captured in a microscopic test chamber. The system includes an electronic circuitry for analyzing the object, and a classification unit for wirelessly communicating with the electronic circuitry.

The classification unit includes a controller for generating a frequency, a first electrode for emitting an alternating electric field from the frequency, a modulator for modulating data into the frequency, a demodulator for demodulating data from the electronic circuitry, and a machine-learning component is coupled to the controller for classifying the pathogens continuously from the demodulated data received from the demodulator.

The electronic circuitry includes a second electrode influenced by the alternating electric field to receive the modulated data from the controller via the first electrode, a converter generates DC energy and a clock from the alternating electric field's charges, a rectifier to separate positive and negative electrical charges from the DC energy, an array of electronic switches to direct the electrical charges.

Further the electronic circuitry includes a sequencer sub-circuit for controlling the array of electronic switches, a communication sub-circuit for demodulating the data, further the communication sub-circuit loads the data into the sequencer sub-circuit, a conductive hollow micro needle to receive charges from the electronic switches, a conductive nano-needle is configured inside the hollow conductive micro needle to form an ion-jet.

Further, the conductive nano-needle receive charges from the electronic switches to emit ions. Further, the ion jet penetrates into the microscopic test chamber and releases ions to react with the pathogens, wherein the pathogens bioelectric charge pattern modulates the ions.

The electronic circuitry further includes a pair of external electrodes is attached to the microscopic test chamber to receive the modulated bioelectric charge pattern, a first instrumentation amplifier is connected to the pair of electrodes to amplify the modulated bioelectric charge pattern, and an analytical sub-circuit for converting the amplified modulated bioelectric charge pattern of the instrumentation amplifier into a digital value, wherein the analytical sub-circuit communicates the digital value to the controller via the communication sub-circuit.

In yet another objective of the present invention, the system further includes a third electrode on the electronic circuitry (test strip) to capacitively couple back to the classification unit. Further, the electronic circuitry and the classification unit analyzes the pathogens in near real time. Further, the electronic circuitry is assembled as a test strip.

In yet another objective of the present invention, the electronic circuitry includes a notification unit to produce notification to signalize status of the pathogens detection. Further, the notification unit releases UV to sterilize the microscopic test chamber. Further, the electronic circuitry is implanted in a living body to detect pathogens.

In yet another objective of the present invention, an apparatus for detecting pathogens is provided. The apparatus includes a microscopic test chamber to capture a pathogen from the object, an electronic circuitry for analyzing the pathogens inside the microscopic test chamber, and a classification unit for wirelessly communicating with the electronic circuitry.

In yet another objective of the present invention, the microscopic test chamber includes a capillary tube having an object inlet for receiving the object, and a cleaning inlet, and a test chamber is connected to the capillary tube for capturing the object for analysis. The ion jet penetrates into the test chamber to release ions.

While a number of features are described herein with respect to embodiments of the inventions; features described with respect to a given embodiment also may be employed in connection with other embodiments. The following description and the annexed drawings set forth certain illustrative embodiments of the inventions. These embodiments are indicative, however, of but a few of the various ways in which the principles of the inventions may be employed. Other objects, advantages, and novel features according to aspects of the inventions will become apparent from the following detailed description when considered in conjunction with the drawings.

BRIEF DESCRIPTION OF DRAWINGS

The annexed drawings, which are not necessarily to scale, show various aspects of the inventions in which similar reference numerals are used to indicate the same or similar parts in the various views.

DETAILED DESCRIPTION OF DRAWINGS

The present disclosure is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

Figure 1:
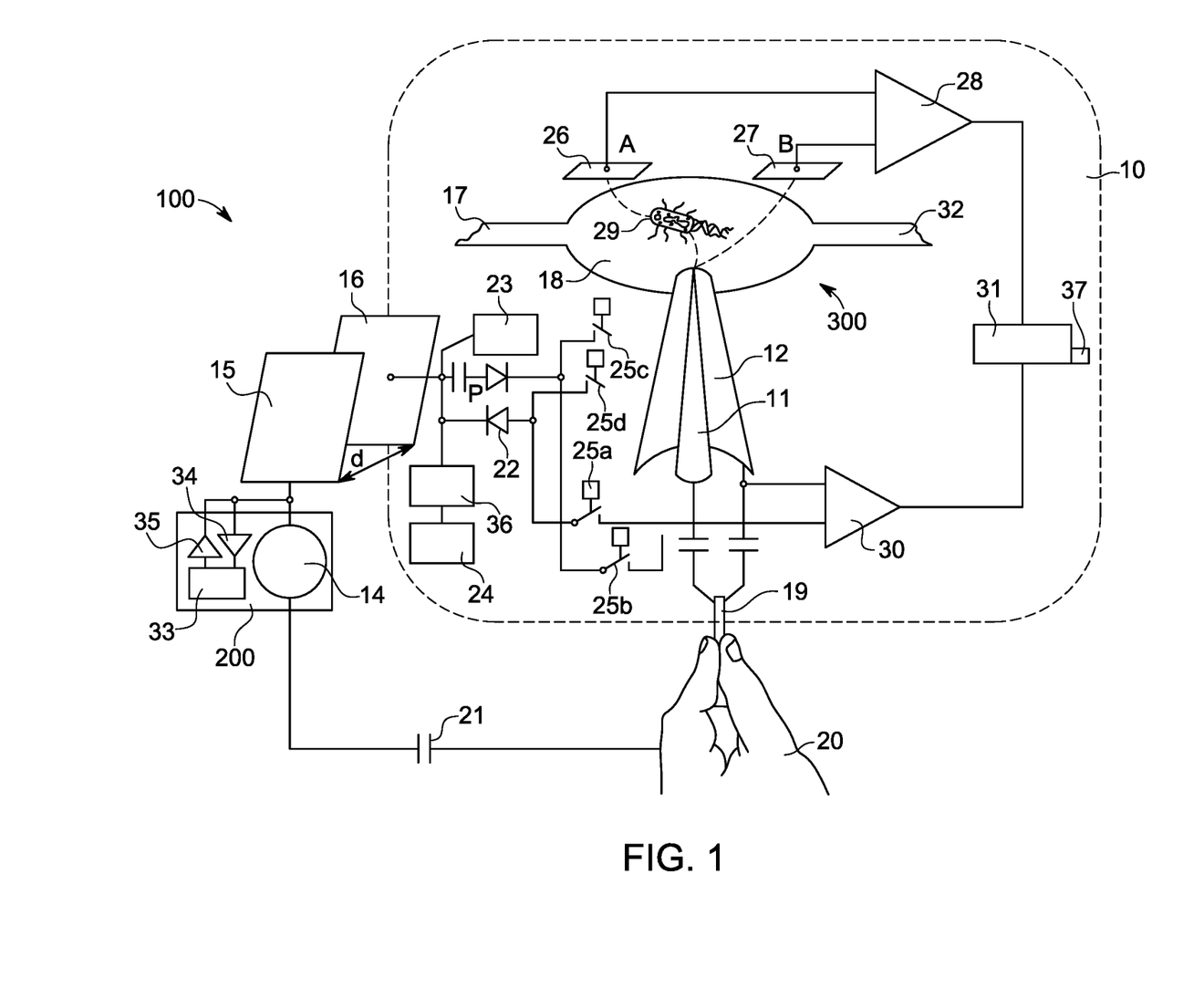
FIG. 1 illustrates a schematic view of a system for detecting and classifying pathogens.

FIG. 1 illustrates a schematic view of the system 100 to rapidly detect and classify pathogens (and other microorganisms) 29. The system 100 detects pathogens in an object. The object is captured in a microscopic test chamber 300. In an embodiment, the object is captured in a microscopic test chamber 300 using capillary forces.

The system 100 includes an electronic circuitry 10 for analyzing the object, and a classification unit 200 for wirelessly communicating with the electronic circuitry 10. Example of the object includes but not limited to a leafy green, water, fruits, and vegetables etc. In another embodiment of the present invention, the electronic circuitry 10 is implanted in a living body to detect pathogens. The electronic circuitry 10 hereinafter termed as test strip, IC Chip, and test strip's IC.

The classification unit 200 includes a controller 14, a first electrode 15, a modulator 35, a demodulator 34, and a machine-learning component 33. The controller 14 generates a frequency. The first electrode 15 emits an alternating electric field from the frequency received from the controller 14. The modulator 35 modulates data into the frequency. The demodulator 34 for demodulating data from the electronic circuitry 10.

Examples of the controller 14 include but not limited to a microcontroller (MCU), CPLD, FPGA etc. with connected peripherals (I/O Ports, UARTS, WiFi, Displays, ADC, DAC, etc.). Examples of the modulator 35 and the demodulator 34 include but not limited to a MOSFET, Transistor, optocoupler, MEMS switch, etc.

The machine learning component 33 is coupled to the controller 14 for classifying the pathogens continuously from the demodulated data received from the electronic circuitry 10. The machine learning component 33 is trained and programmed to monitor and record/store the identification of pathogens in the object.

The machine learning component 33 continuously monitors the analysis performed by the controller to detect the presence of the pathogen specific patterns and records the analysis for future references for quick identification of the pathogens. Examples of the machine learning component 33 include but not limited to a CNN-, KNN-, Markov-, Pascal triangle-, Bayes-, or Numpy algorithm, neuronal computing accelerators, GPU, Turing machines, etc.

The electronic circuitry 10 includes a second electrode 16, a converter 23, a rectifier 22, an array of electronic switches 25a, 25b, 25c, 25d, a sequencer sub-circuit 24, a communication sub-circuit 36, a conductive hollow micro needle 12, a conductive nano-needle 11, a pair of external electrodes 26, 27, a first instrumentation amplifier 28, and an analytical sub-circuit 31.

The second electrode 16 is influenced by the alternating electric field to receive the modulated data from the controller 14 via the first electrode 15. In another embodiment, the second electrode 16 therefore mirrors the field's alternating electric charges. The converter 23 generates DC energy and a clock from the alternating electric charges.

The rectifier 22 separates positive and negative electrical charges from the DC energy. In an embodiment, the converter 23 generates DC energy with different potentials (e.g. +/−10V). Examples of the converter 23 include but not limited to switched (MOS) transistors, diodes, Greatz bridges, etc. and examples of the rectifier 22 include but not limited to (ideal) diodes, phase controlled electronic (MOS) switches, Schottky, Greatz, etc.

The array of electronic switches 25a, 25b, 25c, 25d direct the electrical charges among the sub-circuits of the electronic circuitry 10. The sequencer sub-circuit 24 controls the array of the electronic switches 25a,25b,25c, 25d. Examples of the electronic switches 25 include but not limited to CMOS transmission gates, MEMS etc., and examples of the sequencer sub-circuit 24 include but not limited to a logic gates, flip-flops, (de-) multiplexers, ADC, DAC, PLL, perceptrons, MAC, ALU, adder, ICU, PLC, memory etc.

The communication sub-circuit 36 demodulates the data. Further, the communication sub-circuit 36 loads the data into the sequencer sub-circuit 24. Examples of the communication sub-circuit 36 include, but not limited to AM/FM/IQ/Phase (de-)modulator, impedance-comparator or switchable load, etc. The conductive hollow microneedle 12 receives charges from the electronic switches 25.

The conductive nano-needle 11 is configured inside the hollow conductive micro needle 12 to form an ion-jet. In an embodiment, the sequencer sub-circuit 24 operates electronic switches 25 to apply equal, polarized or alternating electrical potential to both the conductive nano-needle 11 and the conductive hollow microneedle 12.

In an embodiment, the conductive nano-needle 11 is charged with a negative potential while the micro-needle 12 is charged with a positive potential, resulting in creation of the ion-jets where cations are created and emitted into the liquid of distilled or deionized water.

The charges are received by the electrodes 26, 27. Pathogens 29 inside the object comes in-between and modulates the charges with a bioelectric pattern typical for their kind. The conductive nano-needle 11 receive charges from the electronic switches to emit ions.

Further, the ion jet penetrates into the microscopic test chamber 300 and releases ions to react with the pathogens 29 inside the object. The pathogens bioelectric charge pattern modulates the ions. The system 100 is able to analyze the pathogens very quickly and in near real time.

Examples of the nano-needle 11 and microneedle 12 include, but not limited to conductive metallic-, crystallic-, or carbon tubes, deuterium etc. Examples of the pathogens include, but not limited to a *Salmonella* sp., *Listeria monocytogenes*, and Verotoxigenic *E. coli*, including O157:H7.

The pair of external electrodes 26, 27 are attached to the microscopic test chamber 300 to receive the modulated bioelectric charge pattern. The first instrumentation amplifier 28 is connected to the pair of electrodes to amplify the modulated bioelectric charge pattern.

The analytical sub-circuit 31 converts the amplified modulated bioelectric charge pattern of the instrumentation amplifier 28 into a digital value. The analytical sub-circuit 31 communicates the digital value to the controller 14 via the communication sub-circuit 36.

In an embodiment, the digital value is extracted using analog sub-circuits and digital sub-circuits (also defined as analog/digital function blocks) of the analytical sub-circuit 31. Examples of the analytical analog sub-circuit function blocks include but not limited to programmable gain amplifier (PGA), OpAMP, instrumentation Amplifier (INA), Filter, Comparator, NTC diode, photo-diode, ADC, DAC, etc.

In another embodiment of the present invention, the microscopic test chamber 300 includes a capillary tube that includes an object inlet 17 and a cleaning inlet 32, and a test chamber 18. The capillary tube allows movement of the object inside and outside of the test chamber 18 through the object inlet 17 and a cleaning inlet 32, respectively.

In an embodiment, the microscopic test chamber 300 may be engraved on the test strip/electronic circuitry 10 or added as a molded polymer (e.g. Polydimethylsiloxane, (PDMS)). Example of the material of capillary tube include but not limited to silicon, glass, PDMS, etc.

The object inlet 17 allows insertion of the object into the test chamber 18 using a liquid (distilled or deionized water). The cleaning inlet 32 allows the insertion of liquid/air to clean the test chamber 18 and blows out through the object inlet 17.

Further, the pathogens 29 may absorb some charges which are measured with the second instrumentation amplifier 30 connected to the needle's 11, 12 base. It would be readily apparent to those skilled in the art that various material, size and types of microscopic test chamber 300 and the capillary tube may be envisioned without deviating from the scope of the present invention.

Both instrumentation amplifiers 28, 30 output to the analytical sub-circuit 31. The analytical sub-circuit 31 modulates the alternating electric field with a digital load telegram which is received by the (de-)modulator 34 from the controller 14 and interpreted from the machine-learning component 33 for classification.

In another preferred embodiment of the present invention, wherein the electronic circuitry 10 is assembled as a test strip. The capillary tube flushes out the pathogens with a cleaning liquid/pressured air, thus allowing the test strip to be used multiple times. The controller 14 commands the modulator 35 to modulate the alternating electric field with data received from the test strip's IC communication sub-circuit 36 and loaded into the sequencer sub-circuit 24.

In another preferred embodiment, the system further comprising a third electrode 19 is mounted on the test strip (electronic circuitry 10) where a user 20 holds it to capacitively 21 couples to the classification unit 200 due to skin conductivity. In another preferred embodiment of the present invention, the electronic circuitry 10 includes a notification unit 37 to produce a notification to signalize status of the pathogens detection. Examples of the notification unit 37 include but not limited to LEDs, opto-electronics, sounds, vibrations etc.

For exemplary purposes, the notification unit 37 produces notification with an intensity directly proportional to the number of pathogens 29 detected in the object. Further the notification unit 37 is a UV light source which releases UV to sterilize the microscopic test chamber.

Figure 2A:
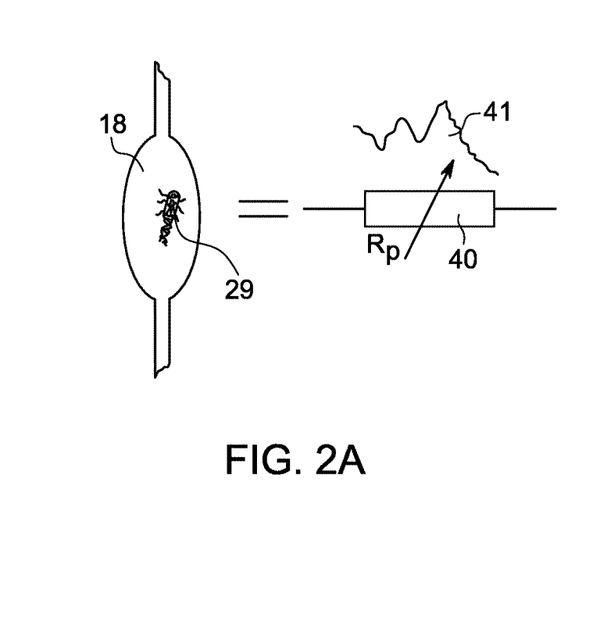
FIG. 2A illustrates a schematic diagram of showcasing pathogens influenced by ions.
Figure 2B:
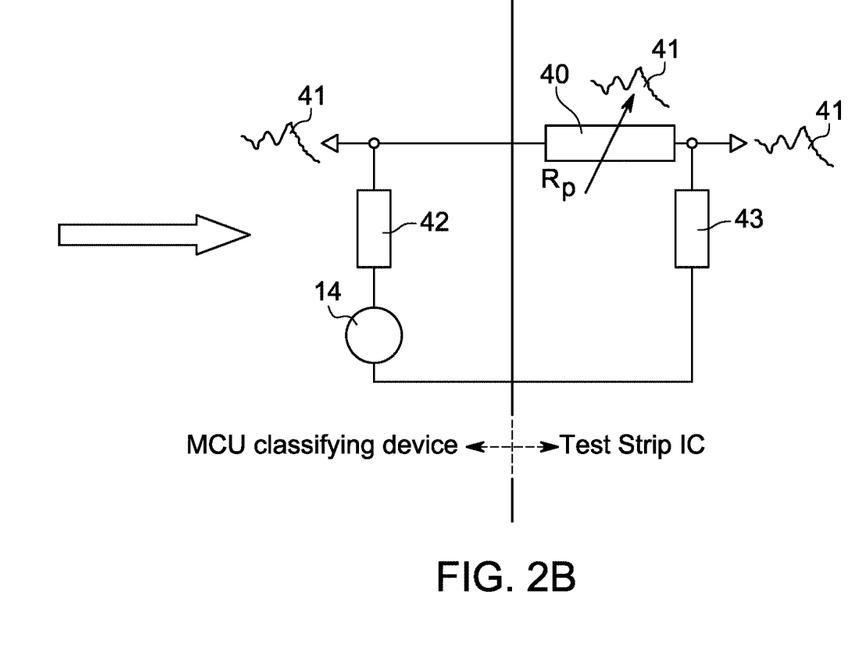
FIG. 2B illustrates another schematic diagram of monitoring impedances of a controller and a test strip IC.

FIG. 2A shows that the pathogens 29 swimming in the examination chamber's 18 liquid (not shown) influenced by ions resemble a variable impedance 40 (Rp) with a pathogen specific pattern 41. This pattern is monitored as changes on either impedance 42 of the MCU (controller 14, shown in FIG. 1) or the test strip IC 43, shown in FIG. 2B. As the resulting values may be too weak to be of significance, they need to be amplified on either side. Therefore, the instrumentation amplifiers 28 and 34 and digitalization (31) shown in FIG. 2C.

Figure 2C:
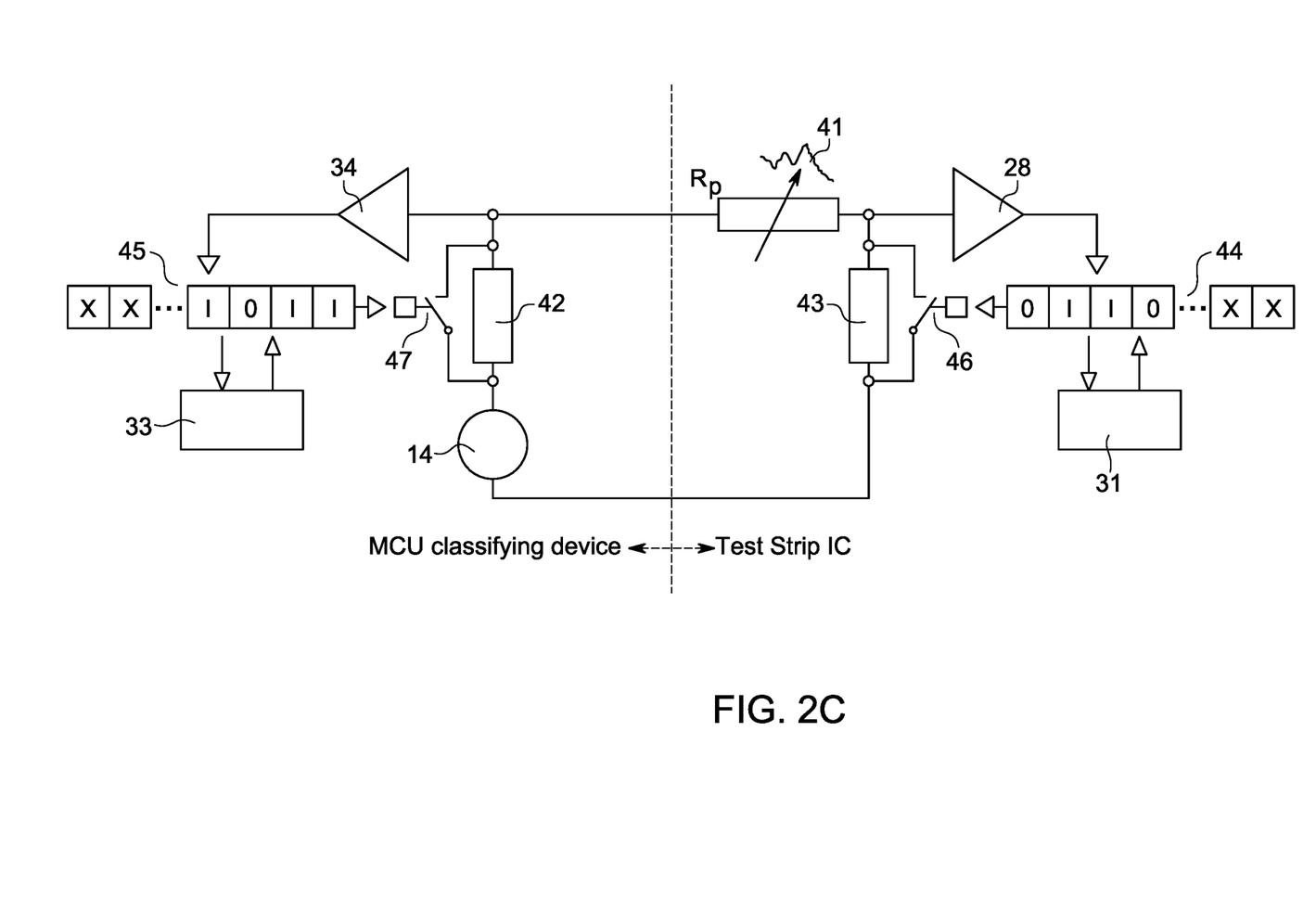
FIG. 2C illustrates another schematic diagram for amplifying values.

The results are stored into shift registers (44,45) that are shifted out to set electronic switches 46,47 that change the impedance on the test strip IC and is received from the MCU's impedance 42 utilizing the alternating electric field as an electron entanglement carrier (not shown). The test strip IC processes this data further (not shown) with filtering (low-pass, high-pass, band-pass, FFT, Goertzel, wavelets, Fourier, etc.).

The MCU has a built-in machine learning algorithms (not shown) to classify the received data and therefore identify the pathogen 29 (shown in FIG. 2A) or provide a probability of the presence of such. It is apparent to those skilled in the art that the same algorithms may be used to teach in new pathogens either during the in-field test or via a network with shared data from other test sides or laboratories, without deviating from the scope of the present invention.

In another embodiment of the present invention, an apparatus for detecting pathogens is provided. The apparatus includes a microscopic test chamber (300, shown in FIG. 1) to capture a pathogen (29, shown in FIG. 1) from the object, an electronic circuitry (10, shown in FIG. 1) for analyzing the pathogen inside the microscopic test chamber (300, shown in FIG. 1), and a classification unit (200, shown in FIG. 1) for wirelessly communicating with the electronic circuitry.

The present invention is a matchbox sized low-cost instrumentation device that provides a weak alternating electric field (AeF) to wirelessly power and communicate with the test strips. The electric field is bi-directionally data-modulated (proprietary phase-duplex) with a patented method.

In an exemplary embodiment, a tiny (<1 mm$^2$) integrated silicon circuit die (IC) is mounted on a test strip. The chip contains an electrical charges energy harvester, as well as routable analog-, digital- and optoelectronic sub-circuits as building blocks for various biochemical sensors.

The test strip resembles a miniaturized biochemical laboratory; all necessary components are integrated to perform i.e. food borne pathogenic bacteria sensing. The test strip is self-calibrating, self-powered, and under permanent control of at least one classification device.

A NTC diode measures temperatures accurately. Every PGA is routable under the control of the sequencer to act like a summing-, differential-, integrator/differentiator amplifier, or as a filter with variable gain in switched capacitor technology. All sub-circuits have compensated transmission gates (e.g. in NMOS/PMOS technology) on in- and outputs, which are controlled by the sequencer block.

The digital sub-circuits (analytical sub-circuit 31, shown in FIG. 1) are a data transceiver block, a sequencer block, an ultra-Turing machine (UTM), a one-bit processor (ICU), as well as a superposition unit (SPU). Another digital block contains e.g. 16 "super registers" (SuRe). Each SuRe contains a serial/parallel input/output shift register. It may turn into an up/down counter or process logical operations with the ICU and is fully controllable by the UTM.

The UTM ultra-Turing machine is a self-propelling unit of e.g. 128 bytes which runs at gate speed (typically 2 ns/operation). It only needs e.g. 16 commands (4 bit) to perform any logical or mathematical task. The SuperPositionUnit digitally performs Bayes' probability—as well as baseline calculation and drift compensation for the electronic circuitry (10, shown in FIG. 1).

The electronic circuitry is coupled to the microfluidic test chamber (e.g. 50 um diameter) with an implemented ion-jet consisting of a nano-needle inside a micro-needle. The details of micro-needle are explained in detail in the U.S. patent Ser. No. 10/241,104, the contents of which are hereby incorporated by reference. Due to capillary effects, pathogens are channeled into the test chamber swimming in a dielectric liquid (e.g. distilled water).

Different potentials on the needles create an ionic beam which entangles with the pathogens. Their biochemical processes are based on electric charge patterns which are filtered and linked to instrumentation amplifiers which output signals as a pathogen specific pattern.

The classification unit has a trained machine model of such patterns to classify the pathogens in seconds with high probability. New species and mutations are identified, recorded and added as they occur. The test strip gets a sequence from the classification unit to create desired food borne pathogenic bacteria sensors (*Salmonella* sp., *Listeria monocytogenes*, Verotoxigenic *E. coli* and O157:H7) temporarily on-the-fly and sends the digitized sensing values radiation-free immediately to the external classification device. Measurements are synched into networks and shared with computers or smart devices based on applications.

In another embodiment of the present invention, using rechargeable (wireless) batteries, the classification unit operates on e.g. 1.5-5V DC. The core of the device is the controller, one of its output pins provides a pulse-width modulated rectangle signal ~500 kHz, which is connected to a flexible electrode via a resonator fork, and results in a weak alternating electric field (AeF) emitted from the electrode.

The electronic circuitry (test strip) in reach (<1 m) couples capacitively (a form of "electron entanglement") with the alternating electric field (AeF) over its surface and the user, and starts operating when in contact with the sample. Therefore, the test strip has conductive zones that act as electrodes.

The test strip's IC has an integrated converter that converts the alternating electric field (AeF) into DC energy (~1 mW) and a precise synchronized operation (system) clock for its sub-circuits. The controller sends a pathogen sensing configuration sequence e.g. by modulating the duty-cycle of the alternating electric field (AeF) frequency, which is securely received by the test strip's data transceiver block and linked to the sequencer sub-circuit.

Thus, the sequencer sub-circuit connects the required sub-circuits via the electronic switches (transmission gates) to resemble e.g. a scanning tunneling microscope (STM) to quickly detect bioelectrical signatures of food pathogens "in field" with no sample preparation or special training. The sensor configuration stays stable until a new sequence is received.

The sensing results are repeatedly encrypted as a payload and, together with a unique identifier (ID), sent back from the data transceiver block to the classification unit by modulating the alternating electric field (AeF) via a subcarrier, divided (or derived) from the system clock. In this case, the conductive material of the test strip acts as a field modulating electrode.

The classification unit's core e.g. is an FCC-certified "WiFi/BLE Node-MCU" (~2$), often used in biochemical and telemedicine applications. It is easily connected to routers, wireless networks, and smart devices (and use their GPS features for cost savings). Adequate I2C peripheral modules like display (5$), speaker (5$), SD data storage (5$) or GPS (7$) are optionally available. The MCU may be programmed in Python with a novel AI (3.0) core for virtual assistance (VPA).

In an exemplary embodiment, the food tester (person/user) may wear the classification unit like a smartwatch. However, it would readily apparent to those skilled in the art that the classification unit may be used anywhere in the farm-to-fork continuum, e.g. placed or attached near the food products, machines and robots, containers, vehicles, storages, shop shelves and kitchens, without deviating from the scope of the present invention.

The IC chip is preferably embedded in a microfluidic polymer test strip which, among others, serves as a linear PTC temperature-impedance sensor. On the bottom of a smaller side, the test strip has a pinhole centered in the middle as the capillary entry for the sample. Another insulated conductive layer serves as an alternating electric field (AeF) electrode. It has a bifilar structure to resist magnetic influence. Additionally, the IC's optoelectronic sub-circuits measure fluorescence and movements (e.g. *E.coli* tumbling).

The optoelectronic sub-circuits consist of IR and UV LED blocks, IR and UV photodiodes, a driver block and a sensitive (around 1 nA) trans-impedance amplifier. Every pathogen signature is measured in at least two different ways to increase confidence in the results. The specially invented novel multi-redundant system brings this idea even further: as an embedded test strip's silicon core costs only less than 5 cents, it is appropriate to integrate two of them in the test strip.

The test strip's silicon core is designed in biomedical grade e.g. 28 nm ultra-low-power mixed signal MEMs technology. While the energy harvester (converter) provides up to 5 mW, the internal consumption is less than 1 mW (if the LEDs are used), and at around 100 uW on average. The harvester also provides e.g. up to 5 kV ESD protection. A Schmitt trigger creates a rectangle system clock from the alternating electric field (AeF). A system counter block derives all necessary timing for the sub-circuits.

The sensing results may be shared with applications, computers and networks to be compared with alternative methods. The test stripes are robust, hygienic, hacker-safe, require no programming (=bug-free), and accept only sequences from the designated classification unit. The classification unit's weak AeF works wirelessly and contactless in a range of about ~1 m from a test strip.

Further, the classification unit may listen to and interpret spoken or other audible commands to keep free from contamination. With a built-in real-time clock of highest accuracy (2 µs), the classification unit records all relevant classifications of food borne pathogenic bacteria with a timestamp. If the classification unit is equipped with a display and/or speaker, the tester may ask for the food borne pathogenic bacteria' status and get a prompt answer.

The classification unit comes preloaded with (yet, not limited to) the biochemical signatures of: *Salmonella* sp., *Listeria monocytogenes*, Verotoxigenic *E. coli* and O157:H7. Once a new biochemical signature is classified, it is uploaded in the machine learning component and also over the communication network through an interface e.g. over the cloud by all concerning classification devices for instant use. The test strips do not need sample preparation as they are self-learning under the control of their designated classification unit.

Multi-redundant elements in a test strip improve the confidence in the measurement results. As batteries contain chemicals and metals that are toxic and harmful to the environment, the invention provides a non-obtrusive battery-free flexible disposable polymer test strip of only environment-friendly material. Further, the test strips are disposed of without any harm to the environment. However, variants of the strips may be suitable for autoclave sterilization.

The test strip does not rely on chemical markers. Therefore, it may be used to check the quality of water, soil, food- and livestock environment or in medical care situations. This is also helpful to contain food-borne diseases. The microfluidic dielectric capillary transport liquid is a distilled water. Variations of the test strips may be label stickers that work through food packages without opening them. Indicators display freshness, contaminations, allergens, etc.

The system is also useful to create evidence of hygienic measures, e.g. in inflammatory hotspots like hospitals, care homes for children and elderly, (poultry) farms, etc. The test strip does not contaminate the classification unit since the communication between both items is based on proprietary electron entanglement over a distance (contactless and wireless) as the effect of the alternating electric field's influential reach.

With a built-in real-time clock of highest accuracy (2 µs), the classification unit records all relevant classifications of food borne pathogenic bacteria with a timestamp. If the classification unit is equipped with a display and/or speaker, the tester may ask for the food borne pathogenic bacteria' status and get a prompt answer. As a variation, the test strip may be illuminated for simpler visual inspection.

Testers do not need special training; machines for food processing or packaging perform automated testing because the system easily adapts to existing production lines. Furthermore, the technology is also useful when creating microorganism cultures or checking their quality and consistency, e.g. for dairy products. Eventually, special variations of test strips are designed to detect viruses and malignant cells.

The above discussed, and subsequently discussed, embodiments of the present system/apparatus will be described further herein below. When the word "invention" or "exemplification of the invention" is used in this specification, the word "invention" or "exemplification of the invention" includes "inventions" or "exemplifications of the invention", that is the plural of "invention" or "exemplification of the invention". By stating "invention" or "exemplification of the invention", the Applicant does not in any way admit that the present application does not include more than one patentable and non-obviously distinct invention, and maintains that this application may include more than one patentable and non-obvious distinct invention. The Applicant hereby asserts that the disclosure of this application may include more than one invention, and, in the event that there is more than one invention, that these inventions may be patentable and non-obvious one with respect to the other.

The abstract of the disclosure is submitted herewith as required by 37 C.F.R. section 1.72(b). As stated in 37 C.F.R. section 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

It should be appreciated that many of the elements discussed in this specification may be implemented in a hardware circuit(s), a circuitry executing software code or instructions which are encoded within computer readable media accessible to the circuitry, or a combination of a hardware circuit(s) and a circuitry or control block of an integrated circuit executing machine readable code encoded within a computer readable media. As such, the term circuit, appliances, apparatus, system, application, or other equivalent description of an element as used throughout this specification is, unless otherwise indicated, intended to encompass a hardware circuit (whether discrete elements or an integrated circuit block), a circuitry or control block executing code encoded in a computer readable media, or a combination of a hardware circuit(s) and a circuitry.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the inventions have been shown and described with respect to a certain embodiment or embodiments, equivalent alterations and modifications will occur to others skilled in the art upon the reading and understanding of this specification and the annexed drawings. In particular regard to the various functions performed by the above describe elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the inventions. In addition, while a particular feature of the inventions may have been described above with respect to only one or more of several illustrated embodiments, such feature may be combined with one or more other features of the other embodiments, as may be desired and advantageous for any given or particular application.

The invention claimed is:

1. A system for detecting pathogens infecting an object, the pathogens captured in a microscopic test chamber, the system comprising:
an electronic circuitry for analyzing the pathogens; and
a classification unit for wirelessly communicating with the electronic circuitry, the classification unit comprising:
a controller for generating a frequency;
a first electrode for emitting an alternating electric field from the frequency received from the controller;
a modulator for modulating data into the frequency;
a demodulator for demodulating data from the electronic circuitry; and
a machine-learning component coupled to the controller for classifying the pathogens continuously from the demodulated data received from the demodulator; and
the electronic circuitry comprising:
a second electrode influenced by the alternating electric field to receive the modulated data from the controller via the first electrode;
a converter generates DC energy and a clock from the alternating electric field;
a rectifier to separate positive and negative electrical charges from the DC energy;
an array of electronic switches to direct charges of the alternating electrical field;
a sequencer sub-circuit to control the array of electronic switches;
a communication sub-circuit for demodulating the modulated data, further the communication sub-circuit loads the demodulated data into the sequencer sub-circuit;
a conductive hollow micro-needle to receive charges of the alternating electric field from the electronic switches;
a conductive nano-needle configured inside the conductive hollow micro-needle to form an ion-jet, further the conductive nano-needle receives charges from the electronic switches to emit ions, further the ion-jet penetrates into the microscopic test chamber and releases ions to react with the pathogens, wherein the pathogens bioelectric charge pattern modulates the ions;
a pair of micro electrodes attached to the microscopic test chamber to receive the modulated bioelectric charge pattern;
a first instrumentation amplifier connected to the pair of electrodes to amplify the modulated bioelectric charge pattern; and
an analytical sub-circuit for converting the amplified modulated bioelectric charge pattern of the instrumentation amplifier into a digital value, further the analytical sub-circuit communicates the digital value to the controller via the communication sub-circuit.

2. The system according to claim 1, wherein the electronic circuitry and the classification unit analyzes the pathogens in near real time.

3. The system according to claim 1, wherein the electronic circuitry is assembled on a test strip.

4. The system according to claim 3, wherein the system further comprises a third electrode on the test strip to capacitively couple back to the classification unit.

5. The system according to claim 1, wherein the electronic circuitry comprising a notification unit to produce notification to signalize status of the pathogens detection.

6. The system according to claim 5, wherein the notification unit releases UV light to sterilize the microscopic test chamber.

7. The system according to claim 1, wherein the electronic circuitry is implanted in a living body to detect pathogens.

8. An apparatus for detecting pathogens, the apparatus comprising:
a microscopic test chamber to capture the pathogens infecting an object;
an electronic circuitry for analyzing the pathogens inside the microscopic test chamber; and
a classification unit for wirelessly communicating with the electronic circuitry, the classification unit comprising:
a controller for generating a frequency;
a first electrode for emitting an alternating electric field from the frequency received from the controller;
a modulator for modulating data into the frequency; and
a demodulator for demodulating data from the electronic circuitry;
a machine-learning component coupled to the controller for classifying the pathogens continuously from the demodulated data received from the electronic circuitry; and
wherein the electronic circuitry comprising:
a second electrode influenced by the alternating electric field to receive the modulated data from the controller via the first electrode;
a converter generates DC and a clock from the alternating electric field;
a rectifier to separate positive and negative electrical charges from the DC;
an array of electronic switches to direct charges of the alternating electrical field;
a sequencer sub-circuit to control the array of electronic switches;
a communication sub-circuit for demodulating the modulated data, further the communication sub-circuit loads the demodulated data into the sequencer sub-circuit;
a conductive hollow micro-needle to receive charges of the alternating electric field charges from the electronic switches;
a conductive nano-needle configured inside the conductive hollow micro-needle to form an ion-jet, further the conductive nano-needle receives charges from the electronic switches to emit ions, further the ion-jet penetrates into the microscopic test chamber and releases ions to react with the pathogens, wherein the pathogens bioelectric charge pattern modulates the ions;
a pair of micro electrodes attached to the microscopic test chamber to receive the modulated bio electric charge pattern;
a first instrumentation amplifier connected to the pair of electrodes to amplify the modulated bio electric charge pattern; and
an analytical sub-circuit for converting the amplified modulated bio electric charge pattern of the instrumentation amplifier into a digital value, wherein the analytical sub-circuit communicates the digital value to the controller via the communication sub-circuit;
wherein the microscopic test chamber comprising:

a capillary tube having an inlet for receiving the pathogens and a cleaning inlet; and a test chamber connected to the capillary tube for capturing the pathogens for analysis, wherein the ion-jet penetrates into the test chamber to release ions.

9. The apparatus according to claim 8, wherein the electronic circuitry and the classification unit analyzes the pathogens in near real time.

10. The apparatus according to claim 8, wherein the electronic circuitry is assembled on a test strip.

11. The apparatus according to claim 10, wherein the system further comprises a third electrode on the test strip to capacitively couple back to the classification unit.

12. The apparatus according to claim 8, wherein the electronic circuitry comprising a notification unit to produce notification to signalize status of the pathogens detection.

13. The apparatus according to claim 12, wherein the notification unit releases UV light to sterilize the microscopic test chamber.

14. The apparatus according to claim 8, wherein the electronic circuitry is implanted in a living body to detect pathogens.

\* \* \* \* \*